US012746063B2

(12) United States Patent
May et al.

(10) Patent No.: US 12,746,063 B2
(45) Date of Patent: Sep. 29, 2026

(54) MICROWAVE ABLATION PROBE HANDLE WITH WATERPROOF GASKET

(71) Applicant: Varian Medical Systems, Inc., Palo Alto, CA (US)

(72) Inventors: Justin May, Austin, TX (US); Virgilio Gomez, Kyle, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 119 days.

(21) Appl. No.: 18/778,315

(22) Filed: Jul. 19, 2024

(65) Prior Publication Data

US 2026/0020906 A1 Jan. 22, 2026

(51) Int. Cl.

*A61B 18/18* (2006.01)
*A61B 17/00* (2006.01)
*A61B 18/00* (2006.01)
*A61B 90/30* (2016.01)

(52) U.S. Cl.

CPC .......... *A61B 18/1815* (2013.01); *A61B 90/30* (2016.02); *A61B 2017/00199* (2013.01); *A61B 2018/00023* (2013.01); *A61B 2018/00178* (2013.01); *A61B 2018/00577* (2013.01); *A61B 2018/0091* (2013.01); *A61B 2018/1823* (2013.01); *A61B 2018/1869* (2013.01); *A61B 2090/306* (2016.02); *A61B 2090/309* (2016.02)

(58) Field of Classification Search

CPC ........... A61B 2018/00005; A61B 2018/00023; A61B 2018/00172; A61B 2018/00178; A61B 2018/0091; A61B 18/18; A61B 18/1815; A61B 2018/1807; A61B 2018/1823; A61B 2018/183; A61B 2018/1838; A61B 2018/1846; A61B 2018/1853; A61B 2018/1861; A61B 2018/1869; A61B 2018/1876; A61B 2018/1884; A61B 2018/1892; A61B 90/30; A61B 2090/306; A61B 2090/309

See application file for complete search history.

(56) References Cited

U.S. PATENT DOCUMENTS 4,901,719 A * 2/1990 Trenconsky ......... A61B 18/042 606/49
2002/0193786 A1* 12/2002 Berube .................. A61B 18/14 606/33
2009/0222001 A1* 9/2009 Greeley ............. A61B 18/1402 606/33
2009/0322034 A1* 12/2009 Cunningham ......... A61B 18/14 29/428
2011/0118723 A1* 5/2011 Turner ............... A61B 18/1815 606/33
2012/0172863 A1* 7/2012 Brannan ............ A61B 18/1815 606/33

(Continued)

*Primary Examiner* — Bradford C. Blaise

(74) *Attorney, Agent, or Firm* — Morgan, Lewis & Bockius LLP; Manita Rawat

(57) ABSTRACT

A microwave ablation probe includes a handle configured to operably couple a supply cable to a probe needle, and a gasket positioned in the handle to seal a joint between the handle and the supply cable. The gasket is configured to allow a predetermined amount of rotation of the supply cable relative to the handle and to prevent rotation of the supply cable relative to the handle of more than the predetermined amount.

18 Claims, 7 Drawing Sheets

(56) References Cited

U.S. PATENT DOCUMENTS

| | | | | |
|---|---|---|---|---|
| 2012/0259329 | A1* | 10/2012 | Decarlo | A61B 18/18<br>606/41 |
| 2017/0143404 | A1* | 5/2017 | Hancock | A61B 46/10 |
| 2020/0096142 | A1* | 3/2020 | Greep | A61M 1/86 |
| 2022/0000554 | A1* | 1/2022 | Hancock | A61B 90/03 |
| 2025/0152229 | A1* | 5/2025 | Ullrich | A61B 18/14 |

* cited by examiner

MICROWAVE ABLATION PROBE HANDLE WITH WATERPROOF GASKET

TECHNICAL FIELD

The disclosure relates to microwave ablation probes. More specifically, the disclosure relates to microwave ablation probes that include a waterproof gasket in the handle.

BACKGROUND

Microwave ablation probes can be used in clinical treatments such as thermal ablation treatments. In such treatments, thermal ablation can be used to destroy undesirable tissue such as malignant cells in a body. A microwave ablation antenna can be included in the probe and be used to deliver Radio Frequency (RF) energy such as microwave energy to a target tissue to heat the target tissue and destroy the target tissue. The microwave ablation antenna can be positioned inside the ablation probe that can position the microwave ablation antenna proximate the target tissue.

The ablation probes are often connected to microwave ablation apparatuses that may generate the microwave signals and/or may supply coolant to moderate the temperature of the ablation probe during use. The supply cables that connect the ablation probes to the ablation equipment are often long and cumbersome and may require manipulation during use. Existing ablation probes and supply cables are difficult to use and may not be easily manipulated by the user. In addition, existing probes and supply cables may be coupled together with connections that do not prevent or minimize damage that may occur to the internal elements of the ablation probes or the flow of electrical signals or coolant to the probe. There exists a need, therefore, for improved probes and/or supply cables to overcome the drawbacks of existing systems.

SUMMARY

The present disclosure is directed to microwave ablation probes that may include a waterproof handle that may include a gasket at one or more locations in the handle to prevent the intrusion of fluids into the handle. The ablation probes may include a gasket positioned at the location of connection of the supply cable to the handle. The gasket may allow limited rotation of supply cable relative to the handle while sealing the interior of the handle from intrusion of fluids. The gasket may also limit over-rotation of the supply cable relative to the handle.

In accordance with some embodiments, a microwave ablation probe may include a handle configured to operably couple a supply cable to a probe needle, and a gasket positioned in the handle to seal a joint between the handle and the supply cable.

In one aspect, the joint is a waterproof seal.

In another aspect, the joint is configured to allow a predetermined amount of rotation of the supply cable relative to the handle.

In another aspect, the joint is configured to prevent rotation of the supply cable relative to the handle of more than the predetermined amount.

In another aspect, the handle includes at least one recess and the gasket includes at least one flange and the flange is sized to sealingly engage in the recess.

In another aspect, the flange includes a central circular portion and at least two lateral wings.

In another aspect, the gasket is configured, upon rotation of the gasket in the handle, to contact the housing of the handle to restrict rotation of the gasket in the handle.

In another aspect, the handle includes a first recess and a second recess spaced apart from each other along an axis of the supply cable and the gasket includes a first flange and a second flange each sized to sealingly engage in the first recess and the second recess, respectively.

In another aspect, the first flange and the second flange each include a central circular portion and at least two lateral wings.

In another aspect, the first flange is oriented substantially parallel to the second flange.

In another aspect, the first flange is spaced apart from the second flange.

In another aspect, a length of the first flange along a first direction aligned with the two lateral wings is greater than a width of the first flange along a second direction perpendicular to the first direction.

In another aspect, the gasket is positioned on a fitting configured to connect to an end of the supply cable.

In another aspect, the fitting includes an annular groove configured to engage a strain relief ring on the end of the supply cable.

In another aspect, the supply cable comprises a power cable, a coolant supply line, and a coolant return line.

In another aspect, the handle includes a housing configured to enclose at least one electronic component.

In another aspect, the handle includes a light emitting diode.

In another aspect, the handle includes a light pipe operably coupled to the light emitting diode, and a perimeter seal positioned around the light pipe.

In some embodiments, a microwave ablation apparatus is provided. The microwave ablation apparatus may include an ablation console with a microwave generator, and a microwave ablation probe coupled to ablation console. The microwave ablation probe may include a supply cable, a handle coupled to the supply cable and to a probe needle, and a gasket positioned in the handle to seal a joint between the handle and the supply cable.

In one aspect, the supply cable is removably coupled to the ablation console.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

Figure 1:
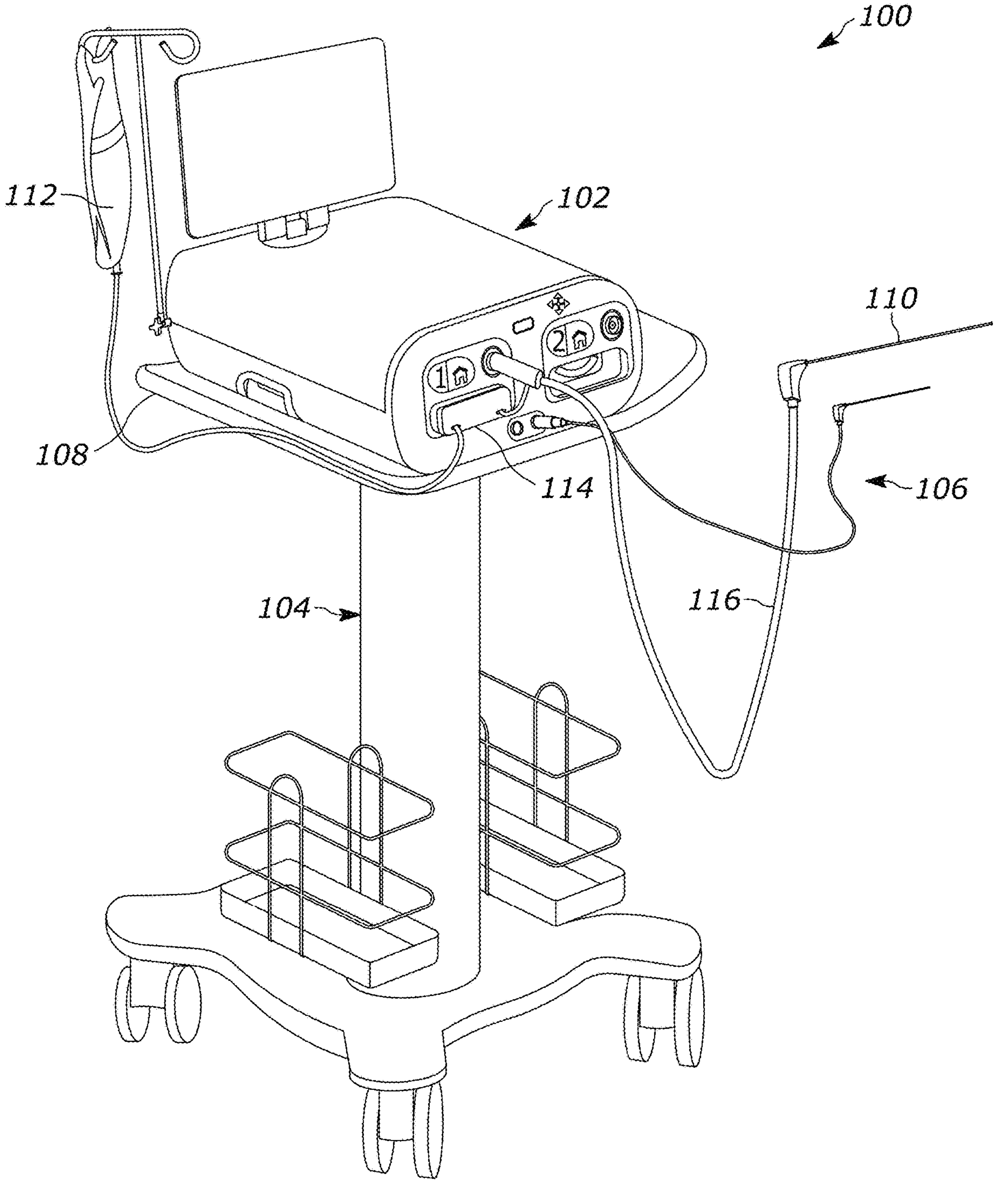
FIG. 1 is an isometric view of an example microwave ablation apparatus in accordance with some embodiments of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The microwave ablation probes of the present disclosure may include a waterproof handle. The ablation probes of the present disclosure may be made waterproof or otherwise resist the intrusion of liquids by including one or more gaskets at possible intrusion locations. One such location for possible intrusion of liquid is at the connection of the ablation probe handle to the cable that delivers the power signal and/or coolant to the ablation probe needle.

In some examples of the present disclosure, a gasket may be included on the cable that fits within one or more recesses in the ablation probe handle. As will be further described below, the gasket may mate with the recesses in the ablation probe handle and prevent the intrusion of liquids into the handle. The interface between the gasket and the handle may allow for some rotation of the cable relative to the handle and prevent undesirable twisting of the cable that may hinder or damage the conveyance of electrical signals or coolant.

The microwave ablation probes of the present disclosure are improvements over existing probes. The ablation probes of the present disclosure may improve the ability of a user of the ablation probes to position and/or manipulate the ablation probe. The ablation probes of the present disclosure may also resist the intrusion of liquids into the handle that may damage or cause disruption to the functionality of the handle.

Turning now to FIG. 1, an example microwave ablation apparatus 100 is shown. In this example, the ablation apparatus 100 includes an ablation console 102, and an ablation probe 110. The ablation console 102 may be portable, in some examples, and may be positioned on a platform 108 of stand 104 to allow the console 102 to be easily moved and positioned as desired during treatment. The console 102 may include a microwave generator that may provide a power signal that is sent to an antenna in the needle of the ablation probe 110. The power signal may be provided to the antenna via a supply cable 116 that may extend from the console 102 to the ablation probe 110. The supply cable 116 may also provide a coolant to the ablation probe 110. The coolant may be a saline solution or other coolant that may be supplied to the ablation probe 110 from a coolant receptacle 112 via a pump cartridge 114 or other pump mechanism.

During an ablation treatment, the needle of the ablation probe 110 may be positioned at or near a target tissue in a patient. A power signal may be supplied to the ablation probe 110 from the console 102. The power signal may be supplied to the ablation probe 110 via the supply cable 116. The power signal may cause microwaves to be emitted from an antenna in the needle of the ablation probe 110. The microwaves may cause the tissue at the needle to be heated to a suitable temperature to destroy the target tissue. A temperature sensor 106 may be positioned at or near the target tissue to measure a temperature that may be achieved at or near the ablation zone.

Figure 2:
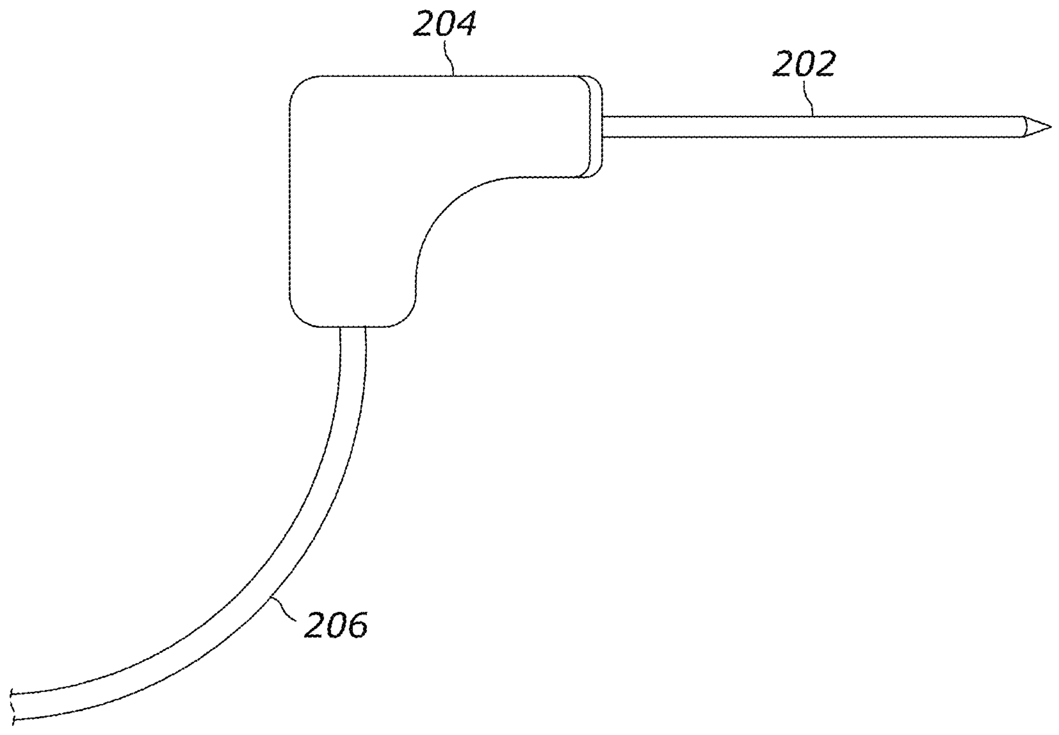
FIG. 2 is an example microwave ablation probe that may include a waterproof handle in accordance with some embodiments of the present disclosure.

Referring now to FIG. 2, an example ablation probe 200 is shown. The ablation probe 200 may be used with the microwave ablation apparatus 100 previously described. The ablation probe 200 may include a needle 202, a handle 204, and a supply cable 206. The ablation probe 200 may be a disposable or single-use probe that is used during a single procedure or for a single patient. In other examples, the ablation probe 200 (or portions of the ablation probe 200) may be re-used.

The needle 202 of the ablation probe 200 may be an elongated member that maybe inserted into a patient at or near the target tissue. The needle 202 may be a metal, alloy or other rigid material. The needle 202 may be cylindrical and pointed. The needle 202 may be hollow such that various elements are positioned inside the needle 202. For example, a power line and an antenna may be located inside needle 202. The power line may be positioned inside the needle 202 to deliver a power signal from a microwave generator to the antenna. Coolant lines may also be positioned inside the needle to deliver coolant to a distal end of the needle 202. The coolant may be used to control a temperature of the needle 202 and/or to control a size and shape of the ablation zone that may be created at the distal end of the needle 202.

The handle 204 may connect and/or operably couple aspects of the ablation probe 200 that are provided from the supply cable 206 to the needle 202. The supply cable 206 may include a power line that delivers the power signal from the microwave generator. The supply cable 206 may also include a coolant supply line and a coolant return line. The coolant supply line may deliver coolant to the needle 202 and the coolant return line may convey the coolant away from the needle 202 after it has been used to cool the needle 202. The supply cable 206 may also include one or more wires that may be provide signals from one or more temperature sensors, thermocouples, flow sensors, or other sensors that may provide information regarding operating characteristics of the ablation probe 200.

The supply cable 206 may be an elongated tube or conduit and each of the power line, the coolant supply line, the coolant return line, and other wires and lines may extend within an outer shell of the supply cable 206. A length of the supply cable 206 may allow a user of the ablation probe 200 to position the needle 202 of the ablation probe 200 as desired and to allow the patient to be moved in and/or out of an imaging device during a treatment. For example, a location of the needle 202 may be determined using CT, MRI, Ultrasound, or other imaging devices before, during, or after treatment is performed. Thus, the supply cable 206 may be sufficiently long to allow these diagnostic procedures to be performed. In some examples, the supply cable 206 is at least 12 feet in length. In other examples, the supply cable 206 is at least 10 feet in length. In other examples, other lengths may be used.

The handle 204 may connect and/or operably couple the supply cable 206 to the needle 202. The power signal, the coolant, and/or sensor signals may be conveyed or delivered from the supply cable 206 to the needle 202 through the handle 204. The handle 204 may include a housing that may enclose various aspects such as fluid connections, electrical connections, electrical components, and the like. The handle 204 may be configured to orient the needle 202 in a desired alignment relative to the longitudinal axis of the supply cable 206. In the example shown, the handle 204 is a right-angle handle. The handle 204 orients the needle 202 at about 90 degrees (or substantially perpendicular) to the longitudinal axis of the supply cable 206. In other examples, the handle 204 may orient the needle 202 at a different angle relative to the longitudinal axis of the supply cable 206.

During an ablation treatment, it may be desirable to have the needle 202 and the supply cable 206 in a right angle or other angled arrangement to allow the needle 202 to be inserted at the target tissue in a patient and allow the supply cable 206 to be easily routed back to the ablation console. In many existing ablation probes, the supply cable 206 is fixed or positively connected to the handle 204. Since wires and or supply lines are routed through the supply cable 206, it may be undesirable to allow rotation of supply cable 206 relative to the handle 204 because if the supply cable 206 and the lines that run through the supply cable 206 are allowed to rotate, the internal lines may become twisted. The twisted lines, in the case of the coolant lines, for example, may cause a restriction of flow. For electrical lines, the twisted lines may cause longitudinal stresses to be imparted on the lines that may cause damage to electrical connections. Still further, when the supply cable 206 and/or the internal lines in the supply cable 206 are twisted to the extent that sufficient stresses are caused in lines, the lines may break.

The ablation probes of the present disclosure allow limited relative rotation between the handle 204 and the supply cable 206. It allows some rotation to allow a user to manipulate and adjust the position of the needle 202 during insertion and use while preventing undesirable twisting of the supply cable 206 that would cause damage or breakage.

Figure 3:
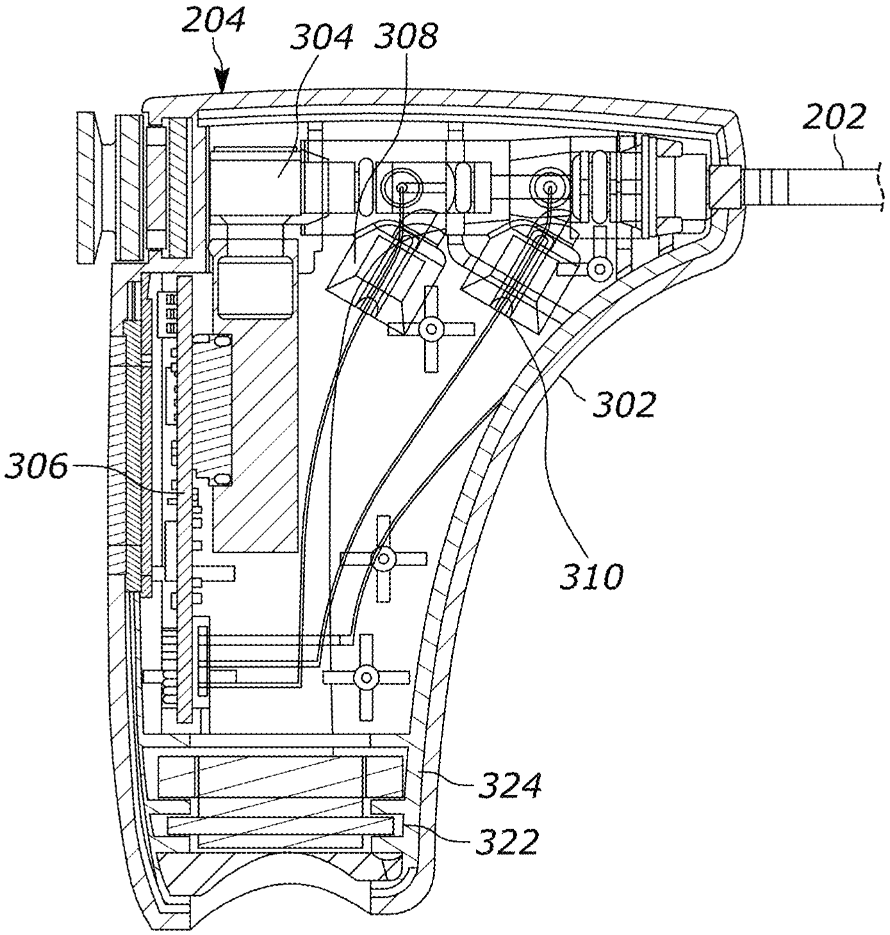
FIG. 3 is a cross-sectional side view of an example microwave ablation handle in accordance with some embodiments of the present disclosure.

Turning now to FIG. 3, a view of the handle 204 is shown. In this example, the handle 204 is shown with a top portion of the housing removed so as to illustrate internal structure and aspects of the ablation probe 200. As shown, the handle 204 may include a housing 302. The housing 302 may be a shell or outer wall that may enclose various aspects of the ablation probe 200. The housing 302 may enclose a connection 304 of the power line in the supply cable 206 to the needle 202. The housing 302 may also enclose a printed circuit board assembly (PCBA) 306. The housing may also enclose a coolant supply connector 308 that may fluidly couple a coolant supply line from the supply cable 206 to a coolant flow path in the needle 202. The housing 302 may also enclose a coolant return connector 310 that may fluidly couple the coolant return line to the coolant flow path in the needle 202. While not all aspects of the ablation probe 200 are listed here, other elements may also be enclosed in the housing 302.

The housing 302 may be made of suitable material such as a plastic, polymer, composite, or the like. The housing 302 may be formed to hold various aspects (such as those previously described) in a desired position in the handle 204. Since the housing 302 may enclose one or more electronic components, such as the PCBA 306, it may be desirable to configure the housing to be waterproof. It may be desirable for the housing to resist and/or prevent the intrusion of external fluids. Therefore, the handle 204 may be sealed to resist the intrusion of external fluids.

Figure 6:
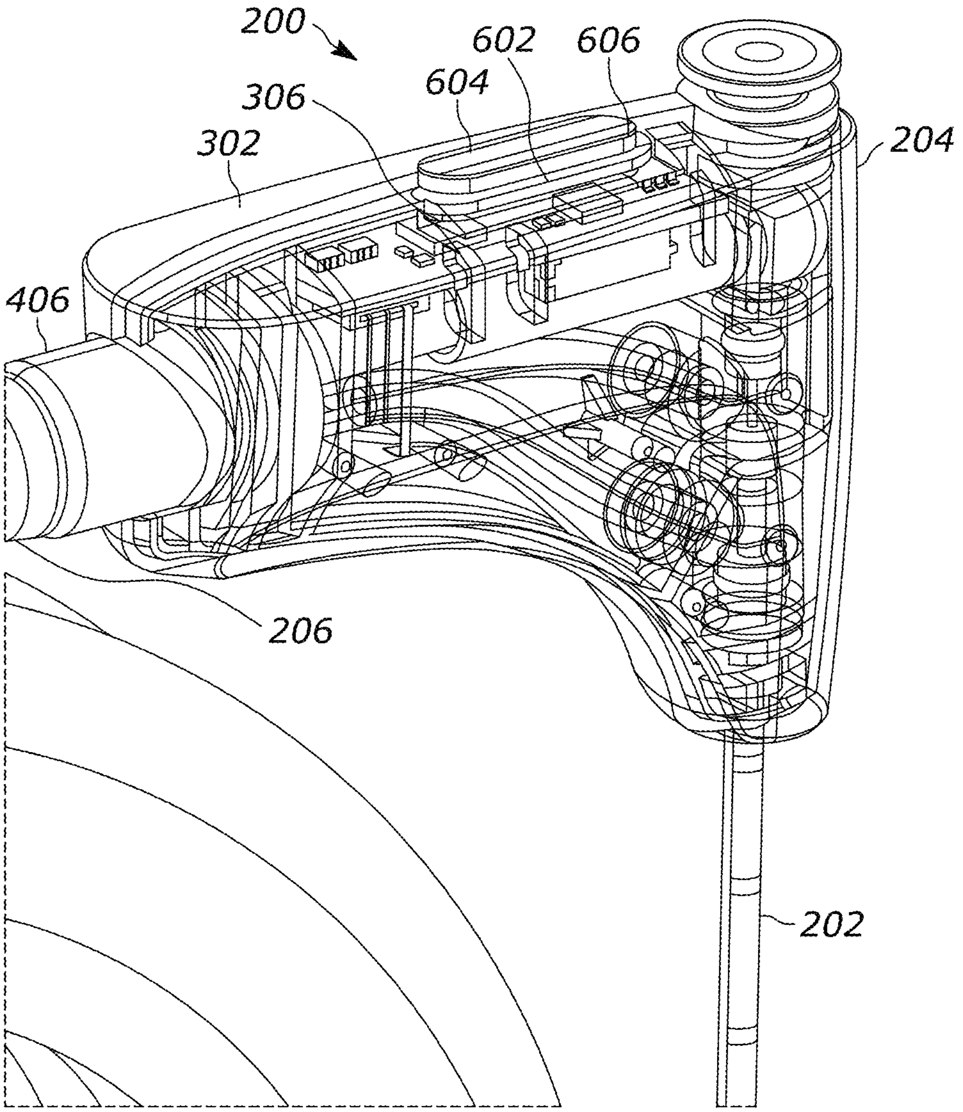
FIG. 6 is an isometric transparent view of the handle of FIG. 3 showing the cable assembled in the handle.

The handle 204 may be made of a top portion and a bottom portion. An example bottom portion of housing 302 is shown in FIG. 3. An example of the housing 302 in which the top portion is connected to the bottom portion of housing 302 is shown in FIG. 6. The bottom portion of housing 302 may be connected to the top portion to seal out the intrusion of fluids. In some examples, the top portion may be ultrasonically welded to the bottom portion. In other examples, other suitable joining methods may be used such as bonding with adhesive, welding, fasteners, and the like.

Despite such connection between the top portion and the bottom portion of the housing 302, there may be locations that may be susceptible to intrusion of liquids. Such locations may include locations of other elements or other connections that are made that access the internal elements of the handle 204.

Figure 4:
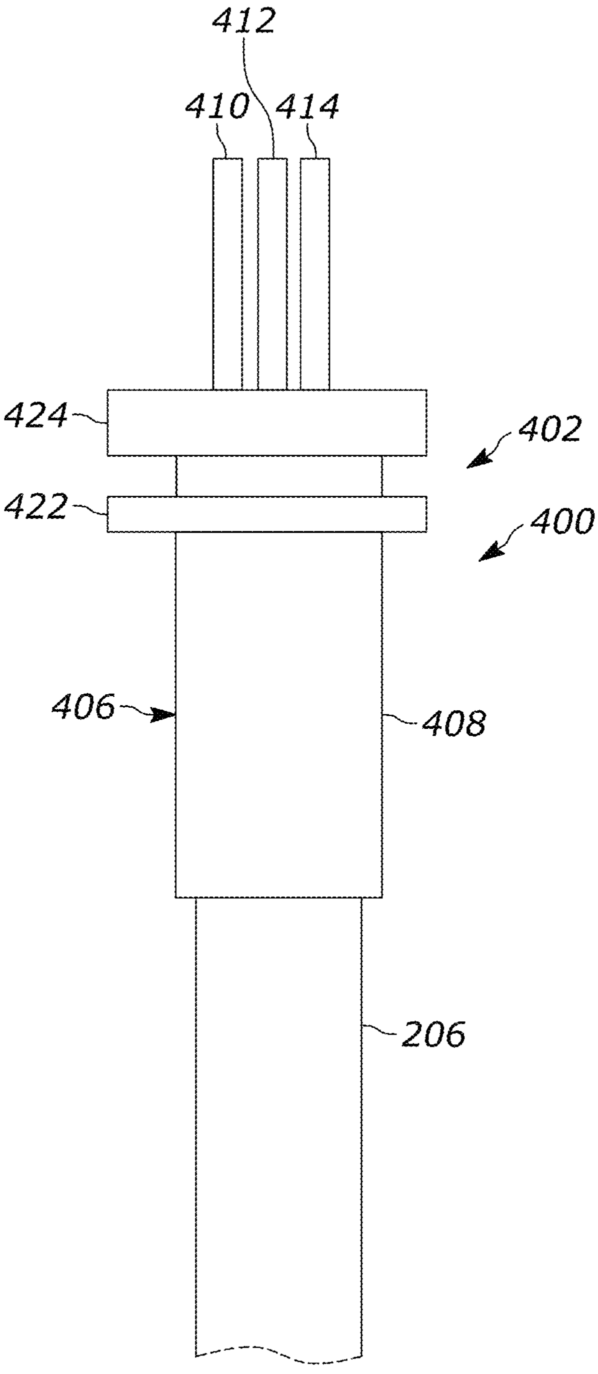
FIG. 4 is a side view of an example ablation cable and end fitting with gasket in accordance with some embodiments of the present disclosure.

One location at which there may be a risk of intrusion of fluids into the handle 204 is at the location at which the supply cable 206 enters the handle 204. To prevent or inhibit the intrusion of fluids at this location, the ablation probe 200 may include a gasket 402 (FIG. 4). The gasket 402 may mate with the handle 204 to prevent or resist the intrusion of fluids into the handle 204. The gasket 402 may also allow for a predetermined amount of rotation of the supply cable 206 relative to the handle 204. The gasket 402 may also prevent over rotation of the supply cable 206 relative to the handle 204.

Referring to FIGS. 3 and 4, the housing 302 may include a first recess 322 and a second recess 324. The first recess 322 and the second recess 324 may be sized and configured and engage with a first flange 422 and a second flange 424 of the gasket 402. The first flange 422 and the second flange 424 may engage with an interference fit to prevent or resist the intrusion of fluid into the handle 204. The first recess 322 and the second recess 324 may be separated from each other along a central axis of the supply cable 206. The first recess and the second recess 324 may be substantially parallel to one another. Similarly, the first flange 422 and the second flange 424 may be separated from each other along a central axis of the supply cable 206. The first flange 422 may be positioned substantially parallel to the second flange 424.

As further shown in this example, the gasket 402 may be located on a fitting 406. The first flange 422 and the second flange 424 may be integrally formed and/or joined to a connector portion 408. The connector portion 408 maybe a cylindrical sleeve that is sized to fit over an end of the supply cable 206. In some examples, the fitting 406 is sized with an interference fit to be retained after it is installed over the end of the supply cable 206. In other examples, the fitting 406 may be fixed to the supply cable using adhesive, welding, staking, or the like.

Figure 5:
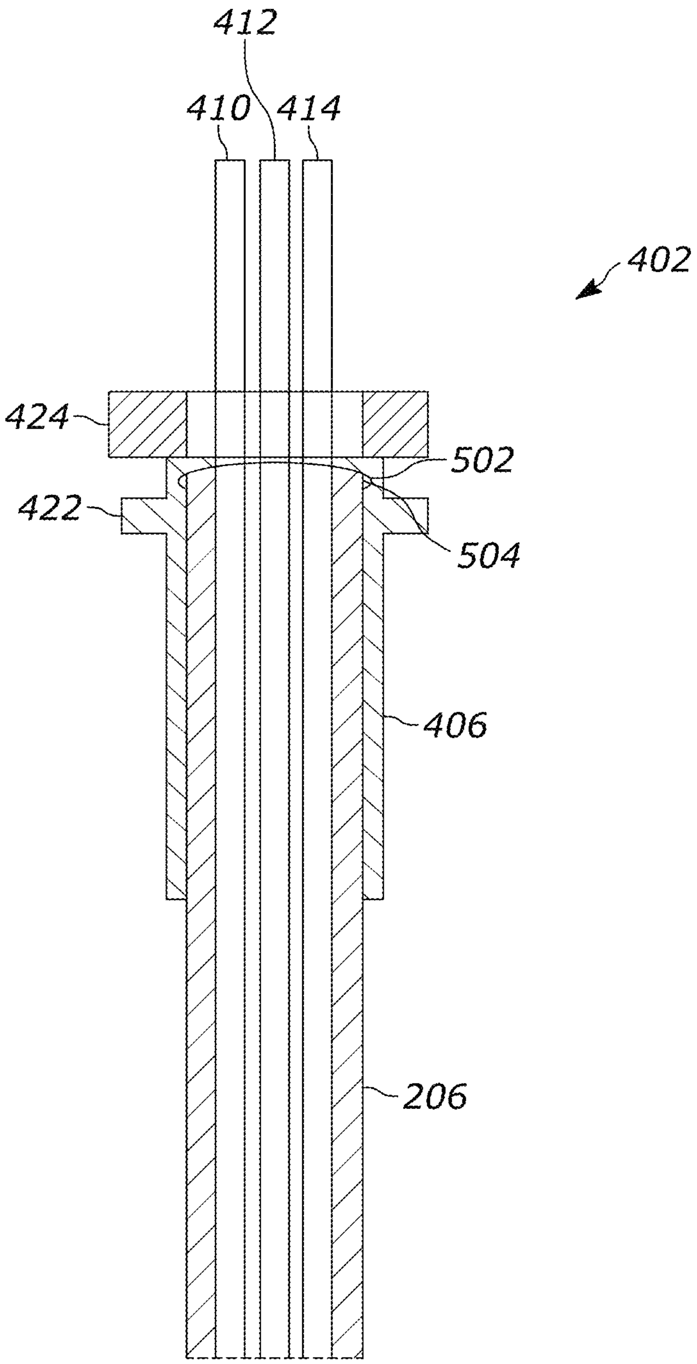
FIG. 5 is a cross-sectional view of the ablation cable of FIG. 4.

As shown in FIG. 5, the fitting 406 may include an annular groove 504 positioned in an internal surface of the inner bore in which the supply cable 206 is inserted. The supply cable 206 may include a ring 502 that is positioned at an end or on the outer surface of the supply cable 206. The ring 502 may provide a strain relief function at the end of the supply cable 206. The ring 502 may be seated into the annular groove 504 of the fitting 406. The interface between the ring 502 and the annular groove 504 may prevent or resist relative movement between the supply cable 206 and the fitting 406, particularly in the longitudinal direction. As further shown, the fitting 406 may allow the power line 410, the supply coolant line 412, the return coolant line 414, and other wires or signal lines (not shown) to extend through the fitting 406 such that they may be coupled to respective connector elements in the handle 204.

As discussed above, the gasket 402 and the recesses in handle 204 may be configured to allow limited relative rotation while limiting excessive relative rotation. Such configuration may allow some manipulation and movement during a treatment but prevent the damage or disruption of flow of electrical signals or coolant from the supply cable 206 to the needle 202.

Figure 7:
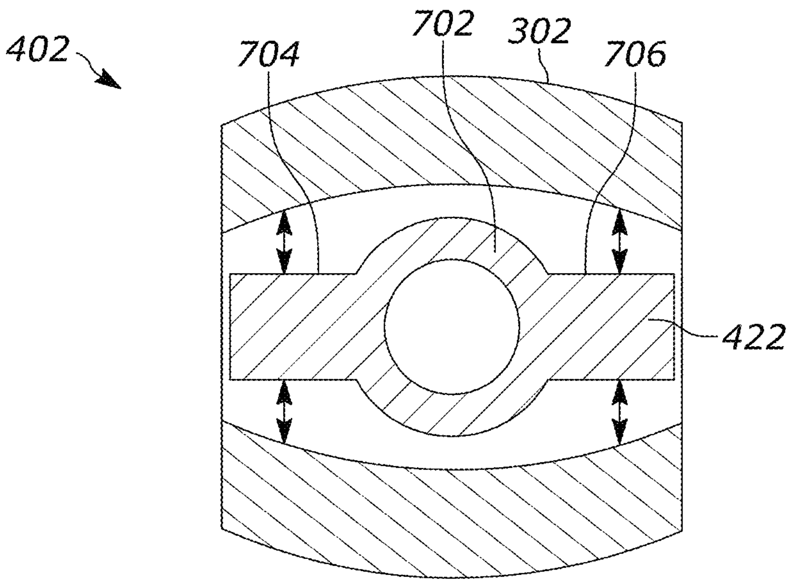
FIG. 7 is a cross-sectional end view of the cable and handle of FIG. 6.

With reference to FIG. 7, in one example, the first flange 422 and/or the second flange 424 may include a central circular portion 702 and a first wing 704 and a second wing 706. The first wing 704 and the second wing 706 may extend laterally outward from opposite sides of the central circular portion 702. The central circular portion 702 may be engaged to the first recess 322 in the housing 302 to resist the intrusion of fluids. The first wing 704 and/or the second wing 706 may be spaced apart from the housing 302. A length of the gasket 402 measured in a direction across the gasket 402 between the first wing 704 and the second wing 706 may be greater than a height of the gasket 402 measured as a height or diameter of the central circular portion 702.

This configuration may allow the gasket 402 to rotate in the housing 302. The supply cable 206 with the gasket 402 attached may rotate in the housing 302 until the first wing 704 and/or the second wing 706 contacts an inner surface of the housing 302. In one example, the spacing and the flexibility of the first wing 704 and the second wing 706 may allow a total rotation of about 70 degrees of the supply cable 206 relative to the handle 204. In other examples, the amount of rotation can be different from this amount. In other examples, the amount of rotation may be predetermined. The amount of allowed rotation may be controlled by varying the amount of spacing between the first wing 70 and the second wing 706 and the housing 302. In other examples, the amount of allowed rotation may be controlled by varying the flexibility or durometer of the material of the gasket 402.

While some rotation is permitted by the configuration of the gasket 402 and the housing 302, over-rotation is prevented. For example, the contact between the first wing 704 and/or the second wing 706 and the housing 302 prevents the gasket 402 (and the supply cable 206) from becoming twisted such that internal connections in the handle 204 are damaged or flow is restricted. While the description above describes an example shape of the first flange 422, it should be appreciated that the second flange 424 and the second recess 324 may have a similar shape and perform similar functionality. In still other examples, only one flange on the gasket 402 may have the lateral wings to allow limited rotation and to resist over-rotation.

As explained above, the handle 204 of the ablation probe 200 may include one or more electrical components. One such electrical component may be the PCBA 306. With reference to FIG. 6, the handle 204 may also include a light emitting diode 602 that may be coupled to the PCBA 306. The light emitting diode (LED) 602 may be illuminated to indicate operation or successful connection of the ablation probe 200 to the console 102, in some examples. The LED 602 may be coupled to a light pipe 604 that may be positioned in the housing 302 of the handle so that the light from the LED can be seen by a user and is displayed externally from the handle 204. Since the light pipe 604 is positioned in the housing 302, there is a risk of intrusion of liquids between the light pipe 604 and the housing 302. To prevent or to resist the intrusion of fluids, the handle 204 may include a perimeter seal 606 positioned around the light pipe 604 and may be compressed between the light pipe 604 and the housing 302 to seal the mating surfaces of these components. The perimeter seal 606 may have an oval shape to correspond to the shape of the light pipe 604 and may be made of a suitable deformable plastic or rubber material.

The handle 204 may also include other seals at other locations of possible ingress of fluids so that the waterproof characteristic of the handle 204 is maintained. Such other locations may include the location of attachment of the needle 202 or other locations.

The following is a list of non-limiting illustrative embodiments disclosed herein:

Illustrative embodiment 1: A microwave ablation probe comprising: a handle configured to operably couple a supply cable to a needle; and a gasket positioned in the handle to seal a joint between the handle and the supply cable.

Illustrative embodiment 2: The microwave ablation probe of illustrative embodiment 1, wherein the seal is a waterproof seal.

Illustrative embodiment 3: The microwave ablation probe of any of illustrative embodiments 1 or 2, wherein the joint is configured to allow a predetermined amount of rotation of the supply cable relative to the handle.

Illustrative embodiment 4: The microwave ablation probe of any of illustrative embodiments 1 to 3, wherein the joint is configured to prevent rotation of the supply cable relative to the handle of more than the predetermined amount.

Illustrative embodiment 5: The microwave ablation probe of any of illustrative embodiments 1 to 4, wherein the handle includes at least one recess and the gasket includes at least one flange, the flange sized to sealingly engage in the recess.

Illustrative embodiment 6: The microwave ablation probe of illustrative embodiment 5, wherein the flange comprises a central circular portion and at least two lateral wings.

Illustrative embodiment 7: The microwave ablation probe of illustrative embodiment 6, wherein upon rotation of the gasket in the handle, at least one of the two lateral wings contacts a housing of the handle to restrict rotation of the gasket in the handle.

Illustrative embodiment 8: The microwave ablation probe of any of illustrative embodiments 1 to 7, wherein the handle includes a first recess and a second recess spaced apart from each other along an axis of the supply cable and the gasket includes a first flange and a second flange each sized to sealingly engage in the first recess and the second recess, respectively.

Illustrative embodiment 9: The microwave ablation probe of illustrative embodiment 8, wherein the first flange and the second flange each comprise a central circular portion and at least two lateral wings.

Illustrative embodiment 10: The microwave ablation probe of illustrative embodiment 8 or 9, wherein the first flange is oriented substantially parallel to the second flange.

Illustrative embodiment 11: The microwave ablation probe of any of illustrative embodiments 8 to 10, wherein the first flange is spaced apart from the second flange.

Illustrative embodiment 12: The microwave ablation probe of any of illustrative embodiments 9 to 11, wherein a length of the first flange along a first direction aligned with the two lateral wings is greater than a width of the first flange along a second direction perpendicular to the first direction.

Illustrative embodiment 13: The microwave ablation probe of any of illustrative embodiments 1 to 12, wherein the gasket is positioned on a fitting configured to connect to an end of the supply cable.

Illustrative embodiment 14: The microwave ablation probe of illustrative embodiment 13, wherein the fitting comprises an annular groove configured to engage a ring on the end of the supply cable.

Illustrative embodiment 15: The microwave ablation probe of any of illustrative embodiments 1 to 14, wherein the supply cable comprises a power cable, a coolant supply line, and a coolant return line.

Illustrative embodiment 16: The microwave ablation probe of any of illustrative embodiments 1 to 15, wherein the handle comprises a housing configured to enclose at least one electronic component.

Illustrative embodiment 17: The microwave ablation probe of illustrative embodiment 16, wherein the handle comprises a light emitting diode.

Illustrative embodiment 18: The microwave ablation probe of illustrative embodiment 17, wherein the handle comprises: a light pipe operably coupled to the light emitting diode, and a perimeter seal positioned around the light pipe.

Illustrative embodiment 19: A microwave ablation apparatus comprising: an ablation console comprising a microwave generator; and a microwave ablation probe coupled to ablation console, the microwave ablation probe comprising: a supply cable; a handle coupled to the supply cable and to a probe needle; and a gasket positioned in the handle to seal a joint between the handle and the supply cable.

Illustrative embodiment 20: The microwave ablation apparatus of embodiment 19, wherein the supply cable is removably coupled to the ablation console.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A microwave ablation probe comprising:

a handle configured to operably couple a supply cable to a needle, wherein the handle includes at least one recess; and a gasket positioned in the handle to seal a joint between the handle and the supply cable, wherein the gasket includes:

at least one flange, the at least one flange sized to sealingly engage in the at least one recess of the handle, and the at least one flange comprises:

a central circular portion; and at least two lateral wings, wherein a length of the at least one flange across the at least two lateral wings is greater than a diameter of the central circular portion of the at least one flange.

2. The microwave ablation probe of claim 1, wherein the seal is a waterproof seal.

3. The microwave ablation probe of claim 1, wherein the joint is configured to allow a predetermined amount of rotation of the supply cable relative to the handle.

4. The microwave ablation probe of claim 3, wherein the joint is configured to prevent rotation of the supply cable relative to the handle of more than the predetermined amount.

5. The microwave ablation probe of claim 1, wherein upon rotation of the gasket in the handle, at least one of the at least two lateral wings contacts a housing of the handle to restrict rotation of the gasket in the handle.

6. The microwave ablation probe of claim 1, wherein the at least one recess comprises a first recess and a second recess spaced apart from each other along an axis of the supply cable and the at least one flange comprises a first flange and a second flange each sized to sealingly engage in the first recess and the second recess, respectively.

7. The microwave ablation probe of claim 6, wherein the first flange and the second flange each comprise a central circular portion and at least two lateral wings.

8. The microwave ablation probe of claim 7, wherein the first flange is oriented substantially parallel to the second flange.

9. The microwave ablation probe of claim 8, wherein the first flange is spaced apart from the second flange.

10. The microwave ablation probe of claim 9, wherein a length of the first flange across the two lateral wings is greater than a diameter of the central circular portion of the first flange.

11. The microwave ablation probe of claim 1, wherein the gasket is positioned on a fitting configured to connect to an end of the supply cable.

12. The microwave ablation probe of claim 11, wherein the fitting comprises an annular groove configured to engage a ring on the end of the supply cable.

13. The microwave ablation probe of claim 12, wherein the supply cable comprises a power cable, a coolant supply line, and a coolant return line.

14. The microwave ablation probe of claim 1, wherein the handle comprises a housing configured to enclose at least one electronic component.

15. The microwave ablation probe of claim 14, wherein the handle comprises a light emitting diode.

16. The microwave ablation probe of claim 15, wherein the handle comprises: a light pipe operably coupled to the light emitting diode, and a perimeter seal positioned around the light pipe.

17. A microwave ablation apparatus comprising:

an ablation console comprising a microwave generator; and a microwave ablation probe coupled to the ablation console, the microwave ablation probe comprising:

a supply cable;

a handle coupled to the supply cable and to a probe needle, wherein the handle includes at least one recess; and a gasket positioned in the handle to seal a joint between the handle and the supply cable, wherein the gasket includes:

at least one flange, the at least one flange sized to sealingly engage in the at least one recess of the handle, and the at least one flange comprises:

a central circular portion; and at least two lateral wings, wherein a length of the at least one flange across the at least two lateral wings is greater than a diameter of the central circular portion of the at least one flange.

18. The microwave ablation apparatus of claim 17, wherein the supply cable is removably coupled to the ablation console.

* * * * *